United States Patent [19]

Zweifel et al.

[11] Patent Number: 4,486,596
[45] Date of Patent: Dec. 4, 1984

[54] 2,3-DIHYDRO-1-BENZOXEPINE-4,5-DICARBOXYLIC ACID ANHYDRIDES

[75] Inventors: Hans Zweifel, Basel; Walter Schilling, Himmelried; Angelo Storni, Rheinfelden; Daniel Bellus, Riehen, all of Switzerland

[73] Assignee: Ciba-Geigy Corporation, Ardsley, N.Y.

[21] Appl. No.: 526,938

[22] Filed: Aug. 29, 1983

Related U.S. Application Data

[60] Division of Ser. No. 349,420, Feb. 16, 1982, Pat. No. 4,424,366, which is a division of Ser. No. 183,905, Sep. 4, 1980, Pat. No. 4,337,200, which is a continuation-in-part of Ser. No. 9,985, Feb. 6, 1979, Pat. No. 4,242,264.

[30] Foreign Application Priority Data

Feb. 8, 1978 [CH] Switzerland .................... 1400/78

[51] Int. Cl.³ .................................. C07D 321/10
[52] U.S. Cl. .................................... 549/239
[58] Field of Search ..................... 549/236, 239

[56] References Cited

U.S. PATENT DOCUMENTS 4,283,509  8/1981  Zweifel et al. ................. 525/289

OTHER PUBLICATIONS

Baddar et al., *Chem. Abstracts*, vol. 85:159747a, (1976).

*Primary Examiner*—Robert Gerstl
*Assistant Examiner*—William A. Teoli, Jr.
*Attorney, Agent, or Firm*—Luther A. R. Hall

[57] ABSTRACT

Anhydrides of formula V

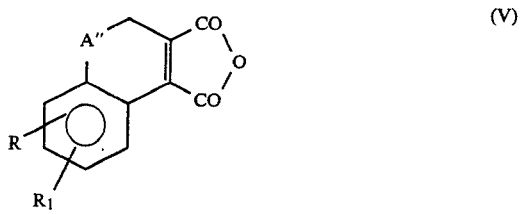

where A" is —OCH$_2$— with the oxygen atom bonded to the aromatic ring and R and R$_1$ independently of one another are hydrogen, halogen, alkyl having 1 to 4 carbon atoms or methoxy are valuable intermediates for the preparation of tricyclic imidyl derivatives. These imidyl derivatives form photocrosslinkable polymers useful for making printing plates and photoresists.

2 Claims, No Drawings

2,3-DIHYDRO-1-BENZOXEPINE-4,5-DICARBOXYLIC ACID ANHYDRIDES

This is a divisional of application Ser. No. 349,420, filed on Feb. 16, 1982, now U.S. Pat. No. 4,424,366, issued on Jan. 3, 1984, which is in turn a divisional of application Ser. No. 183,905, filed on Sept. 4, 1980, now U.S. Pat. No. 4,337,200, issued on June 29, 1982, which in turn is a continuation-in-part of application Ser. No. 9,985, filed on Feb. 6, 1979, now U.S. Pat. No. 4,242,264, issued on Dec. 30, 1980.

The present invention relates to novel tricyclic imidyl derivatives and processes for their preparation. The tricyclic imidyl derivatives according to the invention are suitable for the preparation of photo-crosslinkable polymers.

It is known from the literature that diversely substituted imides, in particular maleimides, are suitable for the preparation of crosslinkable (curable) polymers. Japanese Published Specification Nos. 50-5376, 50-5377, 50-5378, 50-5379 and 50-5380 describe generically different α-arylmaleimides and N-substituted derivatives thereof which are suitable for the preparation of photo-crosslinkable polymers; the said derivatives can be further substituted in the β-position by a halogen atom, a cyano group or a lower alkyl group and the said alkyl group can also form a ring together with the C atom in the ortho-position of the α-aryl group. The specific disclosure is restricted, however, to α-phenylmaleimides and α-phenyl-β-cyano-maleimides and N-substituted derivatives thereof. In Japanese Published Specifications Nos. 49-128,991, 49-128,992, 49-128,993, 50-9682, 50-10884 and 50-77363, the preparation of photo-crosslinkable polymers, for example by reacting N-substituted α-arylmaleimides of the abovementioned type, which have hydroxyl, amino, carboxylic acid or carboxylic acid chloride groups on the N-substituent, with polymers containing corresponding functional groups, is described. Further imidyl derivatives and photo-crosslinkable polymers containing imidyl groups in end or side positions, especially maleimide, dimethylmaleimide, nadicimide and tetrahydrophthalimide groups, are known from German Offenlegungsschriften Nos. 2,031,573, 2,032,037 and 2,626,795.

These previously known imides and the crosslinkable polymers which can be prepared therefrom have the disadvantage of a relatively low photochemical sensitivity and for this reason they are not suitable, or not very suitable, for numerous applications for which highly photosensitive substances are required, or they require the additional use of known photosensitisers, such as benzophenone, thioxanthone and the like. Furthermore, some of these previously known imides are also not very suitable for building up polymers by polymerisation or polycondensation of corresponding monomers.

The object of the invention was, therefore, to provide novel highly photosensitive substances which have a high UV absorption and, because of this, also ensure a high rate of crosslinking even without the addition of photosensitisers and are very suitable for building up polymers by polymerisation or polycondensation, if desired together with suitable comonomers.

The novel compounds have the formula I

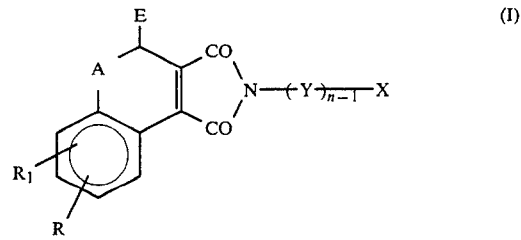

in which n is the number 1 or 2, R and $R_1$ independently of one another are hydrogen, halogen, alkyl having 1-4C atoms or methoxy, A is —$CH_2$—, —$CH_2CH_2$— or —$OCH_2$— with the oxygen atom bonded to the aromatic ring and E is hydrogen, or A is —O— and E is —$CH_3$, and Y is alkylene having 1-30C atoms, which can be interrupted by hetero-atoms, or is cycloalkylene having 5 or 6C atoms, a dicyclohexylmethane radical, arylene having 6-10C atoms, or aralkylene or alkylarylene having 7 or 8C atoms, it being possible for the said radicals Y also to be substituted, and X, when n=1, is a group of the formulae —NH—CO-alkylene or

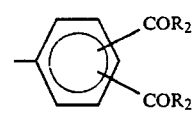

and, when n=2, is —OH, —$NH_2$, —NH-alkyl having 1-4C atoms, —SH, —COOH, —COCl, —CO—O-alkenyl, —O-alkenyl, —O—CO-alkenyl, —NH—CO-alkenyl or —S—CO-alkenyl, the two —$COR_2$s are bonded to the benzene ring in the meta- or para-position relative to one another and the $R_2$s are each —OH, —Cl, alkoxy having 1-4C atoms or phenoxy, or the two —$COR_2$s are bonded to the benzene ring in the ortho-position relative to one another and one of the $R_2$s is —OH or —$O^-M^+$ and the other is

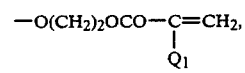

or the two $R_2$s together are —O—, and $M^+$ is an alkali metal cation, a pyridinium cation or a trialkylammonium cation having 3-24 and especially 3-12C atoms, $Q_1$ is hydrogen or methyl and q is an integer from 2 to 4, and alkenyl moieties in the above groups have 2-4C atoms and, when n=2 and Y=—$CH_2$—, A is a radical which differs from —$CH_2$—.

The formula I comprises compounds of the formulae Ia and Ib

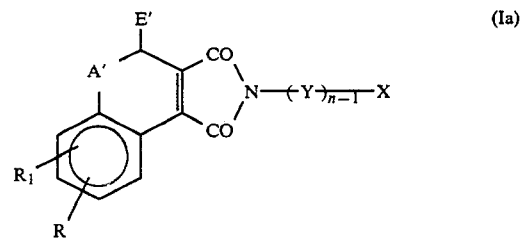

and

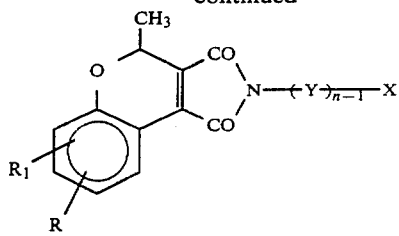

in which A' is —CH₂—, —CH₂CH₂— or —OCH₂— with the oxygen atom bonded to the aromatic ring and E' is hydrogen, R, R₁, X, Y and n are as defined under formula I and, when n=2 and Y=—CH₂—, A' is a radical which differs from —CH₂—.

The compounds of the formula Ia can be prepared by reacting a compound of the formula II

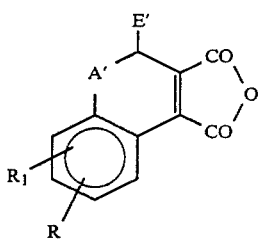

with a compound of the formula III

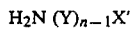

in which formulae A' and E' are as defined under formula Ia and R, R₁, Y and n are as defined under formula I and X', when n=1, is a group of the formula

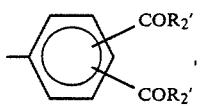

in which the —COR₂' groups are bonded to the benzene ring in the meta- or para-position relative to one another and the R₂'s are each —OH, —O⁻M⁺, alkoxy having 1–4C atoms or phenoxy and M⁺ is as defined under formula I, or in which the —COR₂' groups are bonded to the benzene ring in the ortho-position relative to one another and the two R₂'s together are —O—, and, when n=2, is —OH, —NH₂, —NH-alkyl having 1–4C atoms, —COOH, —SH or —O-alkenyl having 2–4C atoms in the alkyl moiety, if necessary cyclising amidocarboxylic acids which have formed as intermediates and then, if desired, converting the imide into a compound of the formula Ia in which X differs from X'.

The compounds of the formula Ib can be obtained by rearranging a compound of the formula I or Ia in which A is —OCH₂— with the oxygen atom bonded to the aromatic ring and R, R₁, X, Y and n are as defined under formula I to a compound of the formula Ib by the action of heat or in the presence of a basic catalyst.

Alkylene, cycloalkylene, dicyclohexylmethane, arylene, aralkylene or alkylarylene groups Y, according to the definition, can be unsubstituted or substituted, for example by alkyl or alkoxy groups each having 1–4C atoms and in particular each having 1 or 2C atoms, nitro groups or halogen atoms, such as chlorine, bromine or fluorine.

Alkylene groups Y can be straight-chain or branched and can contain one or more hetero-atoms, especially S or O atoms. Unsubstituted, straight-chain or branched alkylene groups are preferred, especially those having 2–11C atoms. Examples of suitable alkylene groups Y are the ethylene group, the 1,3- or iso-propylene group, the 2,2-dimethylpropylene group, the tetramethylene group, the hexamethylene group, the octamethylene group and the decamethylene group.

A cycloalkylene group Y is preferably unsubstituted. It is especially the 1,3-cyclohexylene group and in particular the 1,4-cyclohexylene group.

Substituted arylene groups Y preferably have only one substituent per ring and this substituent is in particular an alkyl or alkoxy group, each having 1–4 and in particular 1 or 2C atoms, or a nitro group. Examples of suitable arylene groups Y are the 1,2-, 1,3- and 1,4-phenylene group, the 1,3-tolylene group, the 5-methoxy-1,3-phenylene group, the 3-nitro-1,4-phenylene group and the 1,7- or 2,7-naphthylene group. Unsubstituted arylene groups are preferred, especially the 1,4-phenylene group and the 1,3-phenylene group.

Aralkylene groups Y are, in particular, the groups

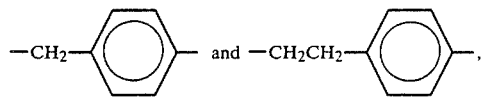

and alkylarylene groups Y are, in particular, the groups

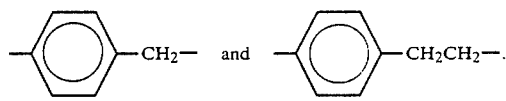

Alkyl or alkoxy groups R, R₁, R₂ or R₂' according to the definition, and also alkyl or alkenyl moieties of substituents X or X' according to the definition, can also be straight-chain or branched.

Examples of alkyl, alkoxy and alkenyl groups according to the definition are: the methyl, ethyl, propyl, isopropyl, n-butyl, tert.-butyl, methoxy, ethoxy, n-propoxy, isopropoxy, n-butoxy, tert.-butoxy, vinyl, allyl and isopropenyl group.

A halogen atom R or R₁ is in particular a chlorine, bromine or fluorine atom. Alkyl groups R and R₁ are advantageously straight-chain and have 1 or 2C atoms. Preferably, however, R and R₁ are each hydrogen.

Alkoxy groups R₂ and R₂' are likewise preferably straight-chain and have 1 or 2C atoms.

M⁺ is, for example, the lithium, sodium, potassium, trimethylammonium, triethylammonium or methyldiethylammonium cation or the tri-n-octylammonium cation. Preferably, M⁺ is an alkali metal cation, especially the sodium cation.

Preferred groups

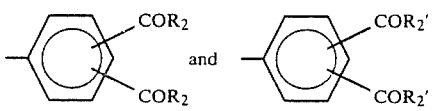

are those in which the groups —COR$_2$ and, respectively, —COR$_2'$ are bonded to the benzene ring in the meta-position relative to one another and the R$_2$s and, respectively, R$_2$'s are each —OH, methoxy, ethoxy, phenoxy or Cl, or those in which the groups —COR$_2$ and, respectively, —COR$_2'$ are bonded to the benzene ring in the ortho-position relative to one another and the two R$_2$s and, respectively, R$_2$'s together are —O—.

Preferred compounds of the formula I and Ia are those in which R and R$_1$ are each hydrogen, A is —CH$_2$—, —CH$_2$CH$_2$— or —OCH$_2$— with the oxygen atom bonded to the aromatic ring, E is hydrogen, Y is straight-chain or branched alkylene having 2-11C atoms, the 1,3- or 1,4-phenylene group or the 1,4-cyclohexylene group and X, when n=1, is a group of the formulae

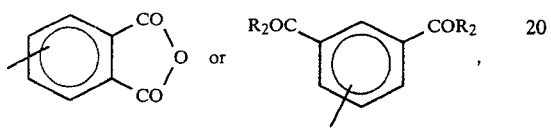

in which the two R$_2$s are each —OH, —Cl, methoxy, ethoxy or phenoxy, and, when n=2, is —OH, —NH$_2$, —COOH, —COCl, —COO-alkenyl, —O-alkenyl or —O—CO-alkenyl and the alkenyl moieties in the said substituents X have 2-4C atoms and are in particular

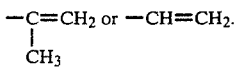

Particularly preferred compounds of the formula I and Ia are those in which R and R$_1$ are each hydrogen, A is —CH$_2$—, —CH$_2$CH$_2$— or —OCH$_2$— with the oxygen atom bonded to the aromatic ring, E is hydrogen, Y is a straight-chain or branched alkylene group having 2-11C atoms and X, when n=1, is a group of the formulae

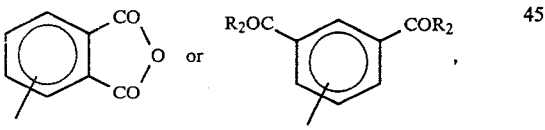

in which the two R$_2$s are each —OH, —Cl, methoxy, ethoxy or phenoxy, and, when n=2, is —OH, —NH$_2$, —COOH or —COCl.

Most particularly preferred compounds of the formula I and Ia are those in which R, R$_1$, Y and X have the preferred meaning defined above, A is —CH$_2$— and E is hydrogen.

Specific preferred compounds of the formula I are compounds of the following formulae X to XVI:

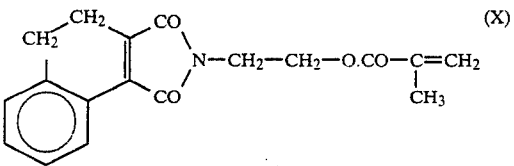

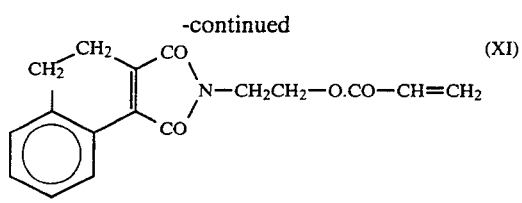

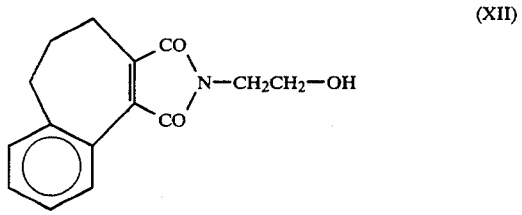

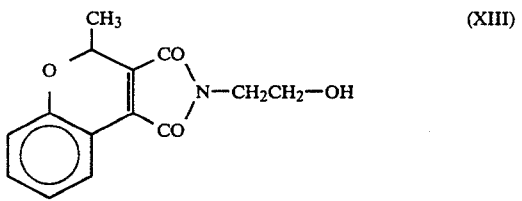

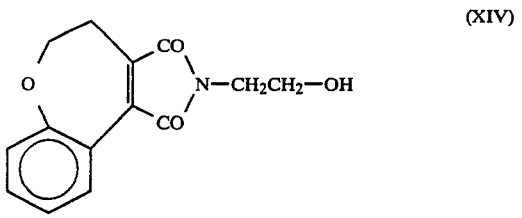

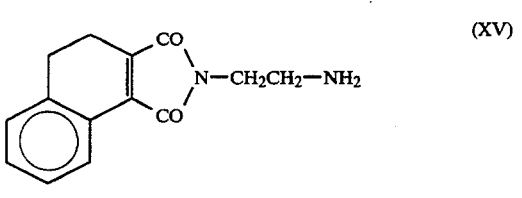

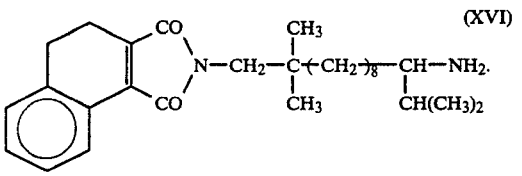

The compounds of the formula III and the compounds of the formula II in which A' is —CH$_2$— and E' is hydrogen are known or can be prepared according to methods known per se. The compounds of the formula II in which A' is —CH$_2$CH$_2$— or —OCH$_2$— with the oxygen atom bonded to the aromatic ring and E' is hydrogen are novel and are also a subject of the invention. The novel compounds of the formula II in which A' is —CH$_2$CH$_2$— and E' is hydrogen can be obtained, for example, by reacting 5-phenylvaleric acid esters, which can be ring-substituted, such as ethyl 5-phenylvalerate, with an oxalic acid diester, for example diethyl oxalate, to give the 3-phenylpropyl-oxaloacetic acid diester and converting the latter into the 6,7-dihydro-5H-benzocycloheptene-8,9-dicarboxylic acid anhydride, which can be ring-substituted, by treatment with a strong acid, such as concentrated sulphuric acid. Compounds of the formula II in which A' is —OCH$_2$— with the oxygen atom bonded to the aromatic ring and E' is hydrogen can be prepared in an analogous manner by reacting phenoxybutyric acid esters, which can be ring-substituted, with an oxalic acid diester and treating the resulting 2-phenoxyethyloxaloacetic acid diester with a strong acid.

Amines of the formula H₂N—Y—O-alkenyl can be obtained, for example, by reacting corresponding aminoalcohols in the presence of bases, such as K₂CO₃, triethylamine or pyridine, with alkenyl halides, especially alkenyl bromides.

Aminobenzenedicarboxylic acids and their derivatives of the formula

can be employed as such or can be prepared in situ by reduction of the corresponding nitrobenzenedicarboxylic acids or derivatives thereof and used further without intermediate isolation. Preferably, the corresponding esters and especially the salts, in particular the alkali metal salts, are used.

The reaction of the amines of the formula III with the anhydrides of the formula II can be carried out in the melt by heating the reactants to temperatures of up to about 250° C., or, alternatively, can be carried out in an aqueous, aqueous-organic or organic medium, in which case the reaction is carried out at temperatures between about 0° C. and the boiling point, depending on the reactants. Preferably, the reaction is carried out in an organic medium.

Advantageously, the anhydride of the formula II is employed in stoichiometric amount or in a slight excess over the amine of the formula III, for example in up to about 20% molar excess.

The organic solvents are in particular aprotic organic solvents. Examples of such solvents are: aliphatic or aromatic hydrocarbons, which can be halogenated, such as methylene chloride, dichloromethane, chloroform, carbon tetrachloride, 1,1,2-trichloroethane, 1,2-dichloroethylene, benzene, toluene and chlorobenzene; anhydrous acetic acid; cyclic ethers, such as tetrahydrofuran, tetrahydropyran and dioxan; cyclic amides, such as N-methyl-2-pyrrolidone, N-acetyl-2-pyrrolidone and N-methyl-ε-caprolactam; N,N-dialkylamides of aliphatic monocarboxylic acids having 1-3C atoms in the acid moiety, such as N,N-dimethylformamide, N,N-dimethylacetamide, N,N-diethylacetamide and N,N-dimethylmethoxyacetamide; N,N,N',N'-tetramethylurea; tetrahydrothiophene dioxide (sulfolane); and dialkylsulphoxides, such as dimethylsulphoxide and diethylsulphoxide.

Mixtures of such solvents can also be employed. Preferred solvents are dioxan, anhydrous acetic acid, methylene chloride, benzene, toluene, xylenes and chlorobenzene.

Depending on the nature of the reactants and on the reaction conditions, in particular at elevated reaction temperatures, the anhydrides of the formula II can be reacted with the amines of the formula III direct, i.e. without additional measures such as treatment with dehydrating agents, to give the imides of the formula Ia. In general, however, amidocarboxylic acids of the formula IV

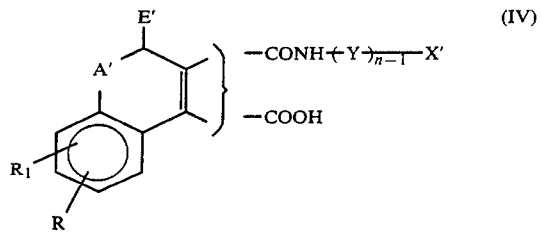

in which n, R, R₁, Y, A', E' and X' are as defined under the formulae I or II and III, are formed as intermediates. These amidocarboxylic acids can be cyclised in a manner known per se, chemically or by the action of heat, to give the imides of the formula Ia, if desired in the presence of an aprotic organic solvent of the abovementioned type.

Cyclisation by the action of heat can be carried out, for example, by heating the reaction product to temperatures of about 50° to 200° C. However, chemical cyclisation using dehydrating agents known per se for imide formation and, where appropriate, anhydride formation is preferred, if necessary in the presence of catalysts, at temperatures of between about 40° and 150° C. The dehydrating agents are, in particular, anhydrides of aliphatic monocarboxylic acids having 2-5 C atoms, which are unsubstituted or substituted by halogen atoms or alkyl groups, such as acetic anhydride, propionic anhydride, butyric anhydride and valeric anhydride, trichloroacetic anhydride and trifluoroacetic anhydride. The preferred dehydrating agent is acetic anhydride. Catalysts which can also be used in the chemical cyclisation are, for example, alkaline earth metal salts or alkali metal salts of aliphatic monocarboxylic acids having 1-3C atoms, such as sodium acetate and potassium acetate.

The compounds obtained according to the invention can, if desired, subsequently be converted to compounds of the formula Ia, in which X differs from X', by methods known per se. Examples are:

1. n=1, X=—NH—CO-alkenyl

By reacting reaction products in which n=1 and X=—NH₂ with acid chlorides alkenyl-COCl.

2. n=1, X=

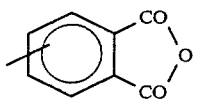

By cyclising compounds of the formula Ia in which n=1 and X=

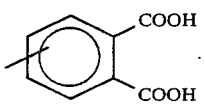

3. n=1, X=

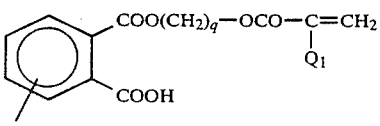

By reacting compounds of the formula Ia in which n=1 and X=

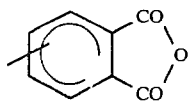

with alcohols

HO—(CH$_2$)$_q$—OCO—C(Q$_1$)=CH$_2$.

4. n=1 and X=

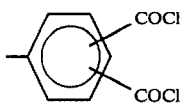

or n=2 and X=—COCl
By reacting compounds of the formula Ia in which n=1 and X=

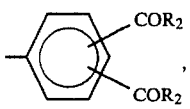

in which the groups —COR$_2$ are bonded to the benzene ring in the meta- or para-position and the two R$_2$s are each —OH or —O$^-$M$^+$, or, respectively, compounds of the formula Ia in which n=2 and X=—COOH, with suitable chlorinating agents, such as thionyl chloride, oxalyl chloride or phosgene.

5. n=2, X=—CO—O-alkenyl
By reacting compounds of the formula Ia in which n=2 and X=—COOH or —COCl with corresponding unsaturated esters or alcohols in the presence of acids or bases.

6. n=2, X=—O—CO-alkenyl or —S—CO-alkenyl
By reacting compounds of the formula Ia in which n=2 and X=—OH or —SH with corresponding unsaturated acids, acid chlorides or esters.

7. n=2, X=—NH—CO-alkenyl
By reacting compounds of the formula Ia in which n=2 and X=—NH$_2$ with acid chlorides alkenyl-COCl.

8. n=2, X=—O-alkenyl
By reacting compounds of the formula Ia in which n=2 and X=—OH with alkenyl halides, especially alkenyl bromides, in the presence of bases, such as K$_2$CO$_3$.

Compounds of the formula Ia in which A is —OCH$_2$— with the oxygen atom bonded to the aromatic ring can be rearranged to compounds of the formula Ib by the action of heat or in the presence of a basic catalyst. The rearrangement is advantageously carried out in an organic solvent, for example an aprotic organic solvent of the abovementioned type, or in anhydrous acetic acid. Rearrangement by the action of heat is advantageously effected by heating the reaction mixture at temperatures of about 80° to 180° C. for about 6 to 48 hours. Compounds of the formula Ia in which X is a non-polymerisable group or in which the substituent X contains a non-polymerisable grouping are particularly suitable for rearrangement by the action of heat.

Rearrangement in the presence of a basic catalyst is advantageously carried out at temperatures of between about 60° and 130° C. and especially between about 80° and 120° C. Compounds of the formula Ia in which X is a polymerisable group or contains such a grouping are particularly suitable for catalytic rearrangement. The bases are, in particular, organic bases, especially tertiary amines of the formula

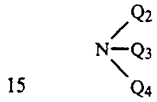

in which Q$_2$ is alkyl having 1–8 C atoms, cycloalkyl having 5 or 6 C atoms, benzyl or phenyl and Q$_3$ and Q$_4$ independently of one another are alkyl having 1–8 C atoms, for example triethylamine, tri-n-butylamine, tri-isopentylamine, tri-n-octylamine, N,N-dimethylcyclohexylamine, N,N-dimethyl-benzylamine, N,N-dimethyl-2-ethylhexylamine and N,N-diethylaniline; tertiary cyclic amines, for example N-alkylmorpholines, such as N-methylmorpholine; N-alkylpiperidines, such as N-methyl- and N-ethyl-piperidine; N-alkylpyrrolidines, such as N-methyl- and N-ethylpyrrolidines; quinuclidine and diazabicyclo[2.2.2]octane; tertiary diamines, such as N,N,N',N'-tetramethylethylene-diamine, N,N,N',N'-tetramethyl-1,3-diaminobutane and N,N'-dimethylpiperazine; and also bicyclic amidines, such as 1,5-diazabicyclo[5.4.0]undec-5-ene, and finally polymeric basic compounds, such as p-dimethylaminomethylpolystyrene.

The amount of catalyst employed can vary within wide limits. In some cases it suffices if the catalyst is present in traces. In general, however, the catalyst is preferably employed in an amount of about 0.1 to 15% by weight, based on the starting compounds of the formula Ia in which A=—OCH$_2$—.

After the reaction has ended, the compounds of the formula I can be isolated in a customary manner and purified if desired.

The compounds of the formula I are valuable intermediates for the preparation of photo-crosslinkable polymers, such as polyesters, polyamides, polyimides, polyester-polyamides, polyethers, polyamines, gelatine, polysaccharides, polycondensates, for example based on phenol-formaldehyde, and homo- and co-polymers which are derived from monomers containing reactive C=C double bonds. Such polymers can be obtained by known synthesis methods for the preparation of macromolecules containing photoactive side groups. In principle, two methods can be used:

1. Incorporation of compounds of the formula I into an existing polymer chain with corresponding functional groups. Compounds suitable for this process are, for example, those of the formula I in which X is —OH, —NH$_2$, —NH-alkyl having 1–4 C atoms, —SH, —COOH or —COCl or in which R$_2$s in the ortho-position together form —O—. Such compounds can be reacted, for example, with polymers containing —NH$_2$, —NH-alkyl,—OH,—COOH,—SH, anhydride or

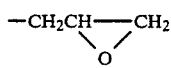

groups and with phenoxy resins containing said OH groups.

2. Build-up of the polymer chain from compounds of the formula I and, if desired, from further monomers, it being possible for the polymer chain to be built up by polymerisation or polycondensation, depending on the nature of the functional groups in the compound of the formula I. Compounds suitable for this process are, for example, compounds of the formula I in which X is as defined when n=1 or compounds of the formula II in which X is —CO—O-alkenyl, —O-alkenyl, —O—CO-alkenyl, —NH—CO-alkenyl or —S—CO-alkenyl when n=2. Compounds of the formula I in which the —COR₂s are bonded to the benzene ring in the meta- or para-position and the R₂s are each —OH, —Cl, alkoxy having 1–4 C atoms or phenoxy, or in which the —COR₂s are bonded to the benzene ring in the ortho-position relative to one another and the R₂s together are —O—, can also be subjected to a polycondensation reaction with diamines, diols, amino-alcohols and, if desired, further di-, tri- or tetra-carboxylic acid derivatives.

Compounds of the formula I in which X is a polymerisable group or contains such a grouping are suitable for homopolymerisation or copolymerisation with other ethylenically unsaturated comonomers, for example vinyl chloride, vinylidene chloride, acrylic acid, methacrylic acid, acrylonitrile, methacrylonitrile, alkyl acrylates and alkyl methacrylates, acrylamide, methacrylamide, styrene, vinylpyridines, ethylene, propylene, vinyl acetate and vinyl propionate, maleates or fumarates or maleic anhydride.

The polymers with side imidyl groups which are thus obtained can be crosslinked under the action of light, especially UV light, and are unsuitable for photomechanical applications, for example for the production of printing plates for the offset printing process, for the production of photo-offset lacquers and for unconventional photography, for example for staining polymer images which are difficult to see after exposure and developing, staining being carried out with suitable dyes, such as oil-soluble dyes or, if the polymer contains acid groups, such as carboxylic acid groups or sulphonic acid groups, cationic dyes. Such polymers are used, in particular, as a so-called photoresist for the production of printed circuits by methods known per se. In this case, the side of the conductor plate provided with the photosensitive layer is exposed through a transparency negative containing the conductor image and then developed, after which the unexposed areas of the layer are removed by developer liquid. Exposure can be carried out with sunlight, carbon arc lamps or xenon lamps. Advantageously, exposure is carried out with mercury high pressure lamps.

EXAMPLE 1

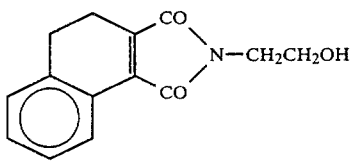

A solution of 70 g (0.35 mol) of 3,4-dihydronaphthalene-1,2-dicarboxylic acid anhydride [prepared according to Org. Syntheses, Col. Vol., 2, 194 (1943)] and 23.5 g (0.385 mol) of ethanolamine in 1.7 liters of glacial acetic acid is kept under reflux for 24 hours. The glacial acetic acid is then removed by distillation, the residue is dissolved in 2 liters of absolute ethanol, 50 g of an ion exchanger ["Dowex 50 W" from Fluka AG] are added and the suspension is kept under reflux for 24 hours. The ion exchanger is then filtered off, the ethanol is distilled off and the residue is recrystallised from diethyl ether/ethanol. This yields 61.8 g (73% of theory) of N-(2′-hydroxyethyl)-3,4-dihydronaphthalene-1,2-dicarboximide; melting point 120.5°–121° C.

IR spectrum (CHCl₃): inter alia 2.93; 5.67; 5.88; 7.0; 7.18; 7.36; 7.61; 9.30; 9.90 μ.

NMR spectrum (CDCl₃): δ=2.7 and 3.02 [2xt, 2x2H, H₂—C(3) and H₂—C(4)]; 3.6 (bs, 4H, 2xCH₂ in the hydroxyethyl group); 7.1–7.4 [m, 3H, H—C(5), H—C(6), H—C(7)]; 8.0–8.2 ppm [m, 1H, H—C(8)].

UV spectrum (C₂H₅OH): λ$_{max}$ (ε)=247 (12,960) and 367 (2,670) nm.

Elementary analysis for C₁₄H₁₅NO₄ (molecular weight 243.27): Calculated: C, 69.12%; H, 5.38%; N, 5.76%. Found: C, 68.95%; H, 5.33%; N 5.74%.

If, in the above example, the residue obtained after distilling off the glacial acetic acid is separated chromatographically on a silica gel column, this yields not only the desired N-hydroxyethyl compound but also the acetate thereof; 103°–105° C. (recrystallised from diethyl ether/n-hexane).

EXAMPLE 2

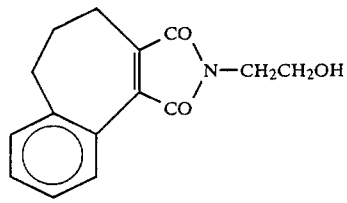

(a) 4.5 g of ethanolamine are added at room temperature (20°–25° C.) to a solution of 15 g (0.07 mol) of 6,7-dihydro-5H-benzocycloheptene-8,9-dicarboxylic acid anhydride in 150 ml of toluene. The mixture is refluxed for 2 hours and the water formed is removed continuously using a water separator. The toluene is then removed by distillation and the residue is recrystallised from ethanol. This yields 1.4 g (82% of theory) of yellow crystals with a melting point of 115° C.

IR spectrum (CHCl₃): inter alia 2.92; 5.67; 5.87; 6.98; 7.12 and 7.36 μ.

Elementary analysis for C₁₅H₁₅NO₃ (molecular weight 257.29): Calculated: C, 70.02%; H, 5.88%; N, 5.44%. Found: C, 70.11%; H, 5.91%; N, 5.60%.

The preparation of 6,7-dihydro-5H-benzocycloheptene-8,9-dicarboxylic acid anhydride is described in paragraphs (b), (c) and (d) below:

(b) Ethyl 5-phenylvalerate

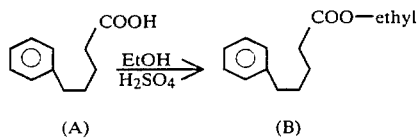

(A)          (B)

250 g (1.4 mols) of 5-phenylvaleric acid are dissolved in 450 ml of absolute ethanol. 114 ml of concentrated sulphuric acid are added to the clear colourless solution and the reaction mixture is refluxed for 48 hours. The reaction mixture, which initially is two-phase, becomes almost homogeneous and separates into two phases again on cooling. The cold two-phase reaction mixture is poured onto diethyl ether and about 1 kg of ice. The aqueous phase is extracted with ether twice more; the ether phases are washed twice with 2N sodium carbonate solution and twice with NaCl solution. The combined ether phases are dried over MgSO$_4$ and the solvent is removed on a rotary evaporator. After drying under a high vacuum at room temperature, 281.7 g of a colourless oil (97.5% of theory) are obtained.

The crude product is used further (cf. paragraph (c)). A sample distilled in a bulb tube at 120°-140° C./0.1 mm Hg is used for characterisation.

NMR spectrum (CDCl$_3$): =7.4–7.0 ppm (5H, m); 4.08 ppm (q, 2H, J=8 Hz); 2.6 ppm (m, 2H); 2.28 ppm (m, 2H); 1.65 ppm (2H, m); 1.02 ppm (3H, t, J=8 Hz).

IR spectrum (CH$_2$Cl$_2$): inter alia 1,740 cm$^{-1}$.

(c) Diethyl 3-phenylpropyl-oxaloacetate

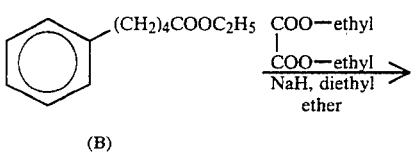

(B)

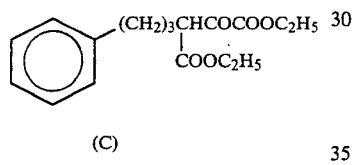

(C)

A suspension of oil-free sodium hydride in diethyl ether, prepared by decanting and twice washing with diethyl ether 71.8 g of a sodium hydride dispersion (55% in oil) in n-pentane under nitrogen and adding 3 liters of absolute diethyl ether, are refluxed. A mixture of 281.7 g (1.36 mols) of ethyl 5-phenylvalerate and 297 g (1.36 mols+50%) of diethyl oxalate is added dropwise to the boiling suspension in the course of about 6 hours. The reaction mixture is then kept under reflux for a total of 66 hours. The thin layer chromatogram (CHCl$_3$) shows, in addition to a very small amount of starting material (R$_f$about 0.6), a main spot with a R$_f$of about 0.5. After cooling, the reaction mixture is poured onto 500 g of ice and 1.05 equivalents of HCl (=530 ml of 2N HCl). The aqueous phase is extracted with diethyl ether, the diethyl ether phase is dried over MgSO$_4$ and the ether is removed in vacuo. After drying in vacuo, 520 g of a reddish oil, which still contains oxalate, are obtained. The crude product is used further direct, since it decomposes with decarbonylation when subjected to purification by distillation.

In addition to the signals of the desired product, the signals of the excess diethyl oxalate are still visible in the NMR spectrum of the crude product.

(d) 6,7-Dihydro-5H-benzocycloheptene-8,9-dicarboxylic acid anhydride

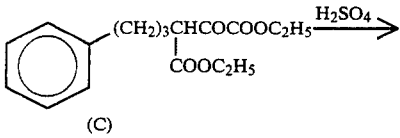

(C)

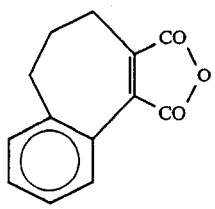

(D)

240 ml of 90% sulphuric acid are cooled to 0°-5° C. 30 g of ester C are added dropwise at this temperature in the course of about 15–20 minutes. A dark yellow to reddish solution forms. The reaction mixture is then allowed to warm to room temperature and the course of the reaction is followed by means of thin layer chromatography. After about 3 to 4 hours no further starting material is visible.

Thin layer chromatogram (CHCl$_3$) starting material: R$_f$about 0.7; reaction product: R$_f$about 0.8.

The reaction mixture is poured onto 1.5 liters of ice and sufficient NaCl to saturate the resulting aqueous phase (about 500 g). With vigorous stirring, a white, crystalline precipitate separates out. This is filtered off with suction, the material on the filter is subjected to strong suction and taken up in diethyl ether and insoluble constituents are separated off. The ether solution is dried over MgSO$_4$, concentrated on a rotary evaporator and dried under a high vacuum. (=1st portion of product D).

The aqueous phase is extracted with diethyl ether and the diethyl ether phase is washed with NaCl solution and dried and the ether is removed on a rotary evaporator. (=2nd portion of product D). On the basis of the thin layer chromatogram, this portion is virtually identical to the first portion.

The two portions are combined and recrystallised from isopropanol. This yields 10 g (47% of theory) of compound D in the form of pale yellowish crystals; melting point 112°–113° C.

EXAMPLE 3

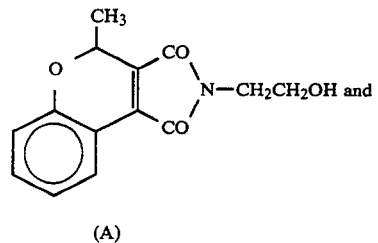

(A)

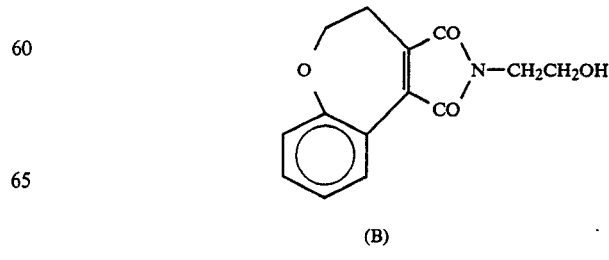

(B)

A solution of 48.65 g (0.2 mol) of 2,3-dihydro-1-benzoxepine-4,5-dicarboxylic acid anhydride and 13.4 g (0.22 mol) of ethanolamine in 1.5 liters of glacial acetic acid is refluxed for 2 days. The glacial acetic acid is then distilled off, the residue is dissolved in 2 liters of absolute methanol, 70 g of an ion exchanger ("Dowex 50 W" from Fluka AG) are added and the suspension is refluxed for 2 days. The ion exchanger is then filtered off, the methanol is removed by distillation and the residue is separated on a silica gel column (solvent system: toluene/ethyl acetate in a volume ratio of 2:1). The first fraction ($R_f$ about 0.3) contains 9.3 g (18% of theory) of N-(2'-hydroxyethyl)-2-methyl-2H-chromene-3,4-dicarboximide (compound A) in the form of yellow crystals (recrystallised from methylene chloride/n-hexane); melting point 124° C.

IR spectrum (KBr): inter alia 2.88; 5.65; 5.83; 6.21; 6.36; 6.90; 7.17; 9.53; 10.0; 13.14μ.

NMR spectrum (CDCl$_3$): δ=1.67 ([d; J=6.5; CH$_3$C(2)]; 3.78 (b"s"; 4H; 2×CH$_2$ in the hydroxyethyl group); 5.46 [t, J=6.5; H—C(2)] and 6.8−7.1+7.2−7.4+7.94 ppm (m+m+d×d; 2H+1H+1H; aromatic H).

UV spectrum (C$_2$H$_5$OH): λ$_{max}$ (ε)=256 (13,370) and 404 (2,920) nm.

Elementary analysis for C$_{14}$H$_{13}$NO$_4$ (molecular weight 259.27): Calculated: C, 64.86%; H, 5.05%; N, 5.40%. Found: C, 64.81%; H, 5.11%; N, 5.40%.

The second fraction ($R_f$ about 0.2) contains 41.5 g (80% of theory) of N-(2'-hydroxyethyl)-2,3-dihydro-1-benzoxepine-4,5-dicarboximide (compound B); melting point 136°-137° C. (recrystallised from CH$_2$Cl$_2$/n-hexane).

IR spectrum (KBr): 2.86; 5.64; 5.86; 6.90; 7.06; 7.62; 9.90; 13.3 and 13.9μ.

NMR spectrum (CDCl$_3$): δ=3.03 [t; J=5; H$_2$—C(3)]; 3.8 (b"s"; 4H; 2×CH$_2$ in the hydroxyethyl group); 4.28 [t; H$_2$—C(2)] and 7.0−7.5+8.67 ppm (m+d×d; 3H+1H; aromatic H).

UV spectrum (C$_2$H$_5$OH): λ$_{max}$ (ε)=248 (12,820), 268 (7,900) and 354 (4,120) nm.

Elementary analysis for C$_{14}$H$_{13}$NO$_4$ (molecular weight 259.27): Calculated: C, 64.86%; H, 5.05%; N, 5.40%. Found: C, 64.76%; H, 5.10%; N, 5.32%.

The starting material (2,3-dihydro-1-benzoxepine-4,5-dicarboxylic acid anhydride) can be prepared as follows:

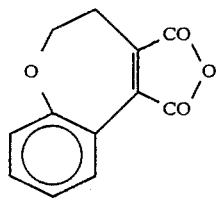

30.8 g (0.10 mol) of crude diethyl 2-phenoxyethyloxaloacetate are allowed to run dropwise in the course of 15 minutes, at a temperature of 5°-10° C., into an ice-cooled mixture of 225 ml of concentrated sulphuric acid and 25 ml of water, with stirring. The reaction temperature is then allowed to rise to 15° C. and the reaction mixture is stirred for one hour at this temperature. The reaction mixture is then poured into a mixture of 1,000 g of ice and 1,500 ml of water, with stirring, whereupon 2,3-dihydro-1-benzoxepine-4,5-dicarboxylic acid anhydride precipitates out. This is filtered off with suction and recrystallised from isopropanol. This yields 14.0 g of 2,3-dihydro-1-benzoxepine-4,5-dicarboxylic acid anhydride (64.7% of theory) with a melting point of 142°-143° C.

The starting material (diethyl 2-phenoxyethyloxaloacetate) for the preparation of the abovementioned anhydride can be prepared as follows:

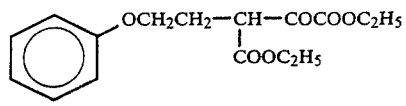

A solution of 22 g (0.15 mol) of diethyl oxalate in 100 ml of diethyl ether is added dropwise, at a temperature of 15° C., to a suspension of 5 g (0.104 mol) of a 50% dispersion of sodium hydride in mineral oil in 50 ml of diethyl ether, with stirring. The reaction mixture is then stirred for 2 hours at room temperature. A solution of 21 g (0.10 mol) of ethyl phenoxy-butyrate [prepared according to Powell and Adams, J. Amer. Chem. Soc., 42, 652 (1920)] in 100 ml of diethyl ether is allowed to run in and the resulting mixture is then refluxed for 10 hours. After cooling, 1 ml of ethanol is added and the mixture is then poured onto a mixture of 100 g of ice and 150 ml of water. The pH of the aqueous phase is adjusted to 3 with 2N hydrochloric acid. The layers are separated in a separating funnel and the aqueous phase is again extracted with 250 ml of diethyl ether. The combined ether extracts are washed with 100 ml of water, then dried over magnesium sulphate and then evaporated under a waterpump vacuum. 30.8 g (100% of theory) of crude diethyl 2-phenoxyethyl-oxaloacetate in the form of a pale reddish oil remain as the residue.

EXAMPLE 4

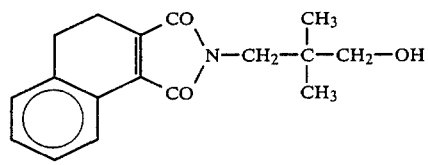

20.0 g (0.1 mol) of 3,4-dihydronaphthalene-1,2-dicarboxylic acid anhydride and 10.3 g (0.1 mol) of 2,2-dimethyl-3-aminopropanol are dissolved in 60 ml of toluene and the solution is refluxed for 2 hours, the water formed being separated off by means of a water separator. After the reaction has ended, the reaction mixture is concentrated to dryness in vacuo at 60° C. The residue is recrystallised from ethanol. This yields 25.1 g (87.9% of theory) of N-(3'-hydroxy-2',2'-dimethylpropyl)-3,4-dihydronaphthalene-1,2-dicarboximide.

Elementary analysis for C$_{17}$H$_{19}$O$_3$N (molecular weight 285): Calculated: C, 71.56%; H, 6.71%; N, 4.91%. Found: C, 70.74%; H, 6.93%; N, 4.75%.

EXAMPLE 5

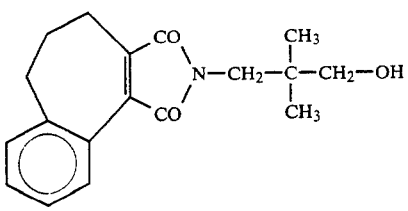

21.4 g (0.1 mol) of 6,7-dihydro-5H-benzocycloheptene-8,9-dicarboxylic acid anhydride and 10.3 g (0.1 mol) of 2,2-dimethyl-3-aminopropanol are dissolved in 60 ml of toluene and the solution is refluxed for 1 hour, the water formed being separated off by means of a water separator downstream of the reaction vessel. After cooling to room temperature, the crystals which have precipitated out are filtered off. This yields 28.9 g (96.6% of theory) and N-(3'-hydroxy-2',2'-dimethylpropyl)-6,7-dihydro-5H-benzocycloheptene-8,9-dicarboximide.

Elementary analysis for $C_{18}H_{21}O_3N$ (molecular weight 299): Calculated: C, 72.22%; H, 7.07%; N, 4.68%. Found: C, 72.07%; H, 7.12%; N, 4.73%.

EXAMPLE 6

24.3 g (0.1 mol) of the N-(2'-hydroxyethyl)-3,4-dihydronaphthalene-1,2-dicarboximide obtained according to Example 1, 12.9 g (0.15 mol) of methacrylic acid, 1.6 ml of concentrated sulphuric acid and 1.0 g of 2,6-ditert.-butyl-p-cresol are dissolved in toluene and the solution is refluxed for 2 hours, the water formed being separated off by means of a water separator downstream of the reaction vessel. The reaction solution is then cooled to room temperature, 5.52 g (0.075 mol) of calcium hydroxide are added and the mixture is stirred thoroughly for 5 minutes. After filtering, the filtrate is concentrated to dryness in vacuo at 60° C. This yields 28.8 g (95.7% of theory) of N-(2'-methacryloyloxyethyl)-3,4-dihydronaphthalene-1,2-dicarboximide.

NMR spectrum: $H_2C=C$ protons at 5.8 and 6.05 ppm (TMS=0).

Elementary analysis for $C_{18}H_{17}NO_4$ (molecular weight 311.33): Calculated: C, 69.45%; H, 5.46%; N, 4.50%. Found: C, 68.65%; H, 5.42%; N, 4.67%.

EXAMPLE 7

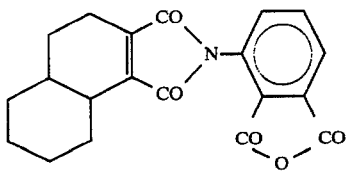

22.3 g (0.1 mol) of disodium 3-aminophthalate and 20.0 g (0.1 mol) of 3,4-dihydronaphthalene-1,2-dicarboxylic acid anhydride are mixed well in a mortar and the mixture is then kept at 140° C. for 2 hours. It is then heated at 160° C. for one hour. After cooling to room temperature, the solid mass is powdered and dissolved at 90° C. in 750 ml of water and, after cooling to about 40° C., the solution is acidified with 220 ml of 1N HCl. The resulting precipitate is filtered off and dried in vacuo at 60° C. The dried product is then dissolved in 750 ml of acetic anhydride and the solution is concentrated to dryness on a rotary evaporator at 70° C. This yields 27.4 g (79.3% of theory) of N-(3'-phthalic anhydride)-3,4-dihydronaphthalene-1,2-dicarboximide.

Elementary analysis: Calculated: C, 69.57%; H, 3.21%; N, 4.06%. Found: C, 65.44%, H, 3.20%; N, 4.44%.

EXAMPLE 8

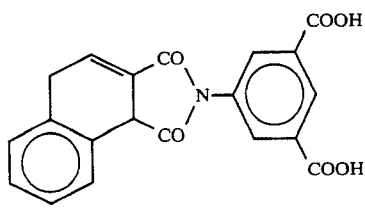

22.6 g of disodium 5-aminoisophthalate, 20.0 g of 3,4-dihydronaphthalene-1,2-dicarboxylic acid anhydride and 100 ml of N,N-dimethylacetamide are added together and the mixture is refluxed for 2 hours, with continuous stirring. The reaction solution is then acidified at a temperature of 80° C. with 220 ml of 1N HCl. After cooling to room temperature, the resulting precipitate is filtered off. The crude product is dried in vacuo at 100° C. This yields 11.9 g (65.6% of theory) of N-(5'-isophthalic acid)-3,4-dihydronaphthalene-1,2-dicarboximide.

Elementary analysis: Calculated: C, 66.12%; H, 3.61%; N, 3.86%. Found: C, 65.34%; H, 3.80%; N, 3.80%.

EXAMPLE 9

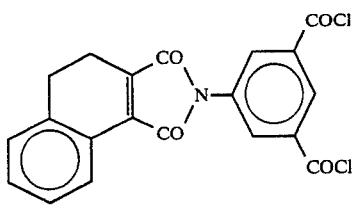

36.3 g (0.1 mol) of the N-(5'-isophthalic acid)-3,4-dihydronaphthalene-1,2-dicarboximide obtained according to Example 8 are refluxed together with 300 ml of thionyl chloride until a clear solution is obtained. About 5 drops of pyridine are added to catalysts the reaction. The reaction product is then evaporated to dryness on a rotary evaporator, an orange-red residue being obtained. 36.7 g (86.5% of theory) of N-(5'-isophthaloyl chloride)-3,4-dihydronaphthalene-1,2-dicarboximide are obtained.

Elementary analysis (after recrystallisation from cyclohexane): Calculated: C, 60.02%; H, 2.77%; N, 3.50%; Cl, 17.72%. Found: C, 60.21%; H, 2.71%; N, 3.47%; Cl, 17.73%.

EXAMPLE 10

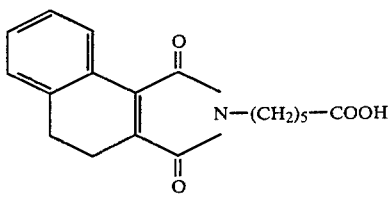

A solution of 20 g (0.1 mol) of 3,4-dihydronaphthalene-1,2-dicarboxylic acid anhydride and 13.1 g (0.1 mol) of 6-aminocaproic acid in 130 ml of acetic acid is refluxed for 6 hours. The reaction solution is evaporated. The yellow solid product, which has a melting point of 109°-111° C., is recrystallised from 100 ml of carbon tetrachloride.

Yield: 23.9 g (76.2% of theory) melting point 108°-111° C., yellow crystals.

Analysis: Calculated: C, 69.00%; H, 6.11%; N, 4.47%. Found: C, 68.78%; H, 6.12%; N, 4.69%.

NMR spectrum (DMSOCH$_6$):=7.9 [1H]; 7.15 [3H]; 3.40 [2H, t]; 3.00 [2H, t]; 2.60 [2H, t]; 2.20 [2H, t]; 1.8–1.1 [6H, Mp].

EXAMPLE 11

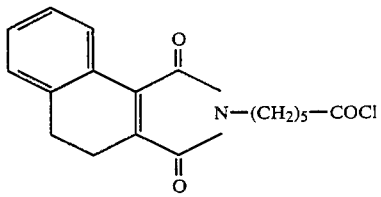

2 g (0.0062 mol) of the N-(caproic acid)-3,4-dihydronaphthalene-1,2-dicarboximide obtained according to Example 10 and 0.51 ml (0.007 mol) of thionyl chloride are dissolved in 10 ml of methylene chloride and the solution is stirred at room temperature for 24 hours. It is then refluxed for 3 hours and then evaporated to dryness. This yields 2 g (94.4% of theory) of an oily product which crystallises after 24 hours. Melting point 65°-67° C.

Analysis: Calculated: C, 65.16%; H, 5.47%; N, 4.22%; Cl, 10.69%. Found: C, 65.34%; H, 5.54%; N, 4.31%; Cl, 9.51%.

EXAMPLE 12

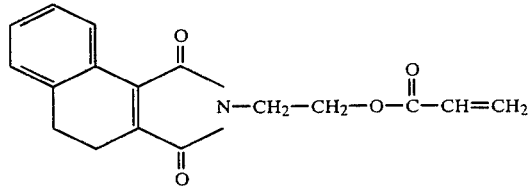

A solution of 60.82 g of N-(2'-hydroxyethyl)-3,4-dihydronaphthalene-1,2-dicarboximide, 24.51 g (0.34 mol) of acrylic acid and 5 ml of chemically pure H$_2$SO$_4$ in 240 ml of toluene, with the addition of 1.2 g of Cu-II acetate, is refluxed for 1½ hours, the water formed (4.5 ml) being separated off by means of a water separator. The solution, which has been cooled to room temperature, is neutralised with 300 ml of 8% NaHCO$_3$ solution. The aqueous phase is extracted with 2×400 ml of toluene. The organic phase is washed with 100 ml of water, dried and evaporated.

Yield: 53.3 g=71.65%, melting point 86°-89° C.

Analysis: Calculated: C, 68.68%; H, 5.09%; N, 4.71%. Found: C, 68.36%; H, 5.1%; N, 4.74%.

EXAMPLE 13

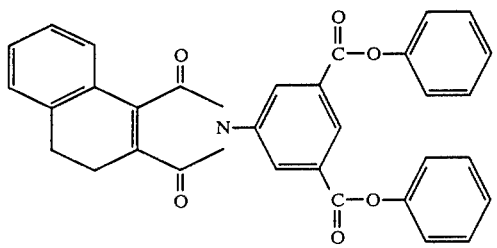

9.5 g (0.100 mol) of phenol are dissolved in 500 ml of anhydrous toluene and the solution is refluxed. 55 ml of toluene are distilled off (drying of the phenol) and the solution is cooled to room temperature. At room temperature, 20 g (0.05 mol) of N-(5'-isophthalic acid dichloride)-3,4-dihydronaphthanlene-1,2-dicarboximide and 10.36 g of triethylamine are added and the mixture is stirred for 50 hours at room temperature. The thick suspension is diluted with 200 ml of toluene and filtered with suction. The yellow filtrate is evaporated and the residue is recrystallised from 70 ml of ethylene glycol monomethyl ether.

Yield: 9 g=35% of theory, melting point 205°-208° C.

Analysis: Calculated: C, 74.56%; H, 4.11%; N, 2.72%. Found: C, 74.41%; H, 3.95%; N, 2.78%.

EXAMPLE 14

16.25 g (0.077 mol) of disodium 3-aminoisophthalate, 150 ml of water, 150 ml of dimethylacetamide and 16.48 g (0.077 mol) of 6,7-dihydro-5H-benzocycloheptene-8,9-dicarboxylic acid anhydride are warmed to 100°, with stirring. The clear solution is stirred at 100° for 1 hour. After cooling to 80°, 85 ml of 2N HCl solution are added dropwise. The yellow suspension, which has been cooled to room temperature, is filtered with suction and the material on the suction filter is washed with 100 ml of cold water and dried in vacuo at 100° for 12 hours. This yields 28 g (96.7% of theory) of N-(3-isophthaloyl-dicarboxylic acid)-6,7-dihydrobenzocycloheptene-8,9-dicarboximide which has the following elementary analysis for the empirical formula C$_{21}$H$_{15}$NO$_6$: Calculated: C, 66.84%; H, 4.01%; N, 3.71%. Found: C, 65.8%; H, 3.97%; N, 3.60%.

EXAMPLE 15

5 g (0.013 mol) of N-(3-isophthaloyldicarboxylic acid)-6,7-dihydrobenzocycloheptene-8,9-dicarboximide, 2 drops of dimethylformamide and 26 ml of thionyl chloride are refluxed for 30 minutes. The red solution is evaporated and the red crystalline product is recrystallised from 30 ml of dry toluene. This yields 2.4 g (43.7% of theory) of N-(3-isophthaloyldicarboxylic acid chloride)-6,7-dihydrobenzocycloheptene-8,9-dicarboxylic acid imide which has a melting point of 178°-181° and the following elementary analysis, calculated for the empirical formula $C_{21}H_{13}NO_4Cl_2$: Calculated: C, 60.89%; H, 3.17%; N, 3.38%; Cl, 17.12%. Found: C, 60.75%; H, 3.21%; N, 3.59%; Cl, 16.9%.

EXAMPLE 16

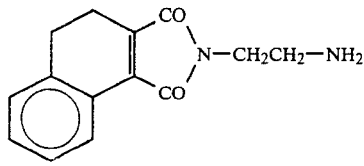

27.6 g of toluene-p-sulphonic acid monohydrate are added to a solution of 27.62 g (0.138 mol) of 3,4-dihydronaphthalene-1,2-dicarboxylic acid anhydride in 300 ml of toluene, followed by 8.69 g of ethylenediamine. The mixture is heated to 60° C. for 30 minutes and then refluxed for 30 minutes, removing continuously the toluene and the water as they are formed by destillation. The residue is dried under vacuo to yield 32.7 g (90.0% of theory) of N-(2'-aminoethyl)-3,4-dihydronaphthalene-1,2-dicarboximide in the form of its toluene-p-sulphonic acid salt. This salt may be purified by recrystallisation from toluene.

In order to set the amino compound free, the salt is suspended in 100 ml of methylene chloride and the suspension is extracted several times with 5% aqueous sodium carbonate solution. After drying the organic phase with anhydrous magnesium sulfate, the solvent is distilled off and the residue, which is the pure N-(2'-aminoethyl)-3,4-dihydronaphthalene-1,2-dicarboximide and has a melting point of 172° C., is dried.

Elementary analysis for the empirical formula $C_{14}H_{14}N_2O_2$: Calculated: C, 69.41%; H, 5.82%; N, 11.56%. Found: C, 68.30%; H, 5.70%; N, 11.30%.

EXAMPLE 17

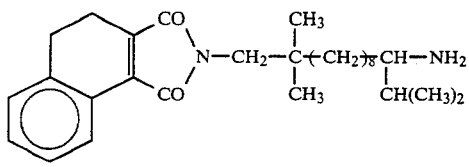

A solution of 27.62 g (0.138 mol) of 3,4-dihydronaphthalene-1,2-dicarboxylic acid anhydride and 37.08 g (0.144 mol) of 1,11-diamino-2,2,12-trimethyltridecane in 300 ml toluene is refluxed for 30 minutes. The solvent and the reaction water are then distilled off and the residue is dried under vacuo. This yields 58.0 g (90.0% of theory) of N-(11'-amino-2',2',12'-trimethyltridecyl)-3,4-dihydronaphthalene-1,2-dicarboximide (melting point 161° C.), which may be recrystallised from toluene.

Elementary analysis for the empirical formula $C_{28}H_{42}N_2O_2$: Calculated: C, 76.67%; H, 9.65%; N, 6.39%. Found: C, 75.20%; H, 10.1%; N, 6.20%.

EXAMPLE 18

100 g of a copolymer of methyl vinyl ether and maleic anhydride (1:1; anhydride content=0.64 mol, average molecular weight 740,000), 77.8 g (0.32 mol) of the N-(2'-hydroxyethyl)-3,4-dihydronaphthalene-1,2-dicarboximide prepared according to Example 1 and 10 ml of pyridine are dissolved in 1,820 ml of dried tetrahydrofuran. The reaction mixture is kept at 80° C. for 72 hours, with stirring. After cooling to room temperature, the clear solution is precipitated in 5 liters of diethyl ether and the precipitate is dried in vacuo. This yields 141.0 g (79.3% of theory) of a white polymer. For elementary analysis, a sample of the polymer is precipitated in 0.1N HCl.

Elementary analysis: Found: C, 55.3%; H, 5.9%; N, 2.23%.

EXAMPLE 19-23

Further crosslinkable polymers are prepared in a manner analogous to that described in Example 18, using:

100 g of the copolymer according to Example 18 and 82.3 g of the imide according to Example 2;

100 g of the copolymer according to Example 18 and 82.9 g of N-(2-hydroxyethyl)-2-methyl-2H-chromene-3,4-dicarboximide;

100 g of the copolymer according to Example 18 and 78.4 g of N-(2'-hydroxyethyl)-2,3-dihydro-1-benzoxepine-4,5-dicarboximide;

100 g of the copolymer according to Example 18 and 87.4 g of N-(3'-hydroxy-2',2'-dimethylpropyl)-3,4-dihydronaphthalene-1,2-dicarboximide; and 100 g of the copolymer according to Example 18 and 95.6 g of N-(3'-hydroxy-2',2'-dimethylpropyl)-6,7-dihydro-5H-benzocycloheptene-8,9-dicarboximide.

EXMPLE 24

10 g of a copolymer of methyl vinyl ether and maleic anhydride (1:1; anhydride content=0.64 mol, average molecular weight 740,000), and 15 g of N-(2'aminoethyl)-3,4-dihydronaphthalene-1,2-dicarboximide prepared according to Example 16 are dissolved in 200 ml of dried tetrahydrofuran. The reaction mixture is kept at 40° C. for 6 hours, with stirring. After cooling to room temperature, the clear solution is precipitated in 2 liters of diethyl ether and the resulting fine polymer powder is dried under vacuo.

A photocrosslinkable polymer is obtained which has an intrinsic viscosity of 0.32 dl/g (in chloroform at 20° C.).

EXAMPLE 25

31.1 g (0.1 mol) of N-(2'-methacryloyloxyethyl)-3,4-dihydronaphthalene-1,2-dicarboximide together with 0.31 g of α,α'-azoisobutyronitrile are dissolved in 140 ml of tetrahydrofuran. The reaction mixture is polymerised under a gentle reflux (about 80° C.) for 6 hours under nitrogen and with continuous stirring. After the reaction has ended, the reaction solution is cooled to room temperature and the polymer is precipitated by adding the reaction solution dropwise to 2 liters of hexane. This yields 24.4 g (78.5% of theory) of a white powder; inherent viscosity: 0.15 dl/g (0.5% by weight in N,N-dimethylformamide at 20° C.).

EXAMPLE 26

2.5 g (0.00662 mol) of N-(3-isophthaloyldicarboxylic acid)-6,7-dihydrobenzocycloheptene-8,9-dicarboximide and 1.75 g of (0.00729 mol) of 1,3-diglycidyl-5,5-dimethylhydantoin are dissolved in 85 ml of cyclohexanone and 1 crystal of tetrabutylammonium chloride is added. The solution is stirred at 110° for 2 hours. The yellow, slightly viscous solution can be used direct for coating copper plates.

EXAMPLE 27

7.3 g (0.0639 mol) of 2,5-dimethylpiperazine and 18 ml of triethylamine are dissolved in 100 ml of dry chloroform in a 750 ml sulphonation flask and the solution is cooled to −5°. At this temperature, a suspension of 8 g (0.0193 mol) of N-(3-isophthaloyldicarboxylic acid chloride)-6,7-dihydrobenzocycloheptene-8,9-dicarboximide and 10.78 g (0.04506 mol) of sebacic acid dichloride in 100 ml of chloroform is added dropwise. The reaction mixture is stirred for 3 hours at room temperature and the slightly viscous solution is precipitated with 1,500 ml of petroleum ether. 13 g of beige polymer are obtained.

EXAMPLE 28

This example relates to images which are produced by photocrosslinking polymers prepared with compounds according to the invention and are rendered more easily visible by staining and to the determination of the relative sensitivity of the images thus obtained. A 400 watt mercury vapour high pressure lamp at a distance of 40 cm from the vacuum table is used for exposure. The original used is a Stauffer step wedge as described in "Photoresist, Material and Processes", W. S. De Forest, page 110 (McGraw-Hill Book Company, New York, 1975).

Coating: The photocrosslinkable polymer is applied to aluminium sheets (about 0.3 mm) by whirler-coating at 1,000 revolutions/minute from a 5% solution in N,N-dimethylformamide.

Developing: 3 seconds in tetrahydrofuran; 30 seconds in 3% $NaHCO_3.H_2O$.

Staining: The polymer which has been crosslinked image-wise can subsequently easily be stained with a cationic dye, for example by staining for 30 seconds in a 5% aqueous solution of the dye of the formula

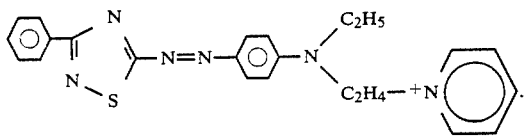

The following table gives the number of stained steps in the step wedge with the corresponding exposure time.

| Polymer according to | Exposure time | Number of stained steps in the step wedge |
| --- | --- | --- |
| Example 18 | 6 minutes | 9 |
|  | 3 minutes | 7 |
|  | 1 minute | 5 |
| Example 19 | 9 minutes | 5 |
|  | 6 minutes | 2 |
|  | 3 minutes | 1 |
| Example 20 | 9 minutes | 5 |
|  | 6 minutes | 3 |
|  | 3 minutes | 1 |
| Example 21 | 9 minutes | 7 |
|  | 6 minutes | 5 |
|  | 3 minutes | 3 |

EXAMPLE 29

Example 28 is repeated except that the photocrosslinkable polymers of Examples 18 to 21 are replaced by the polymer of Example 24. The results are recorded in the following table.

| Exposure time | Number of stained steps in the step wedge |
| --- | --- |
| 6 minutes | 9 |
| 3 minutes | 8 |
| 1 minute | 6 |

What is claimed is:
1. A compound of the formula V

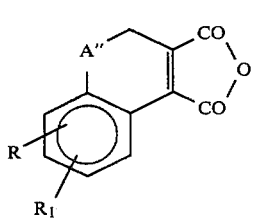

in which A" is —$OCH_2$— with the oxygen atom bonded to the aromatic ring and R and $R_1$ independently of one another are hydrogen, halogen, alkyl having 1–4 C atoms or methoxy.

2. The compound according to claim 1 which is 2,3-dihydro-1-benzoxepine-4,5-dicarboxylic acid anhydride.

* * * * *